United States Patent [19]

Madsen et al.

[11] Patent Number: 4,954,954

[45] Date of Patent: Sep. 4, 1990

[54] APPARATUS FOR GENERATING A BALANCED CALORICALLY LIMITED MENU

[76] Inventors: Lamar R. Madsen, 1570 East Ave., Vernonia, Oreg. 97064; Maki Myoga, 7610 SW. Leslie St., Portland, Oreg. 97223

[21] Appl. No.: 769,353

[22] Filed: Aug. 26, 1985

[51] Int. Cl.⁵ .................................................. G06F 9/00
[52] U.S. Cl. .............................. 364/413.29; 364/922; 364/922.4; 364/927
[58] Field of Search ... 364/200 MS File, 900 MS File, 364/413, 413.29, 413.01

[56] References Cited

U.S. PATENT DOCUMENTS

| | | | |
|---|---|---|---|
| 4,151,668 | 5/1979 | Hungerford | 40/495 |
| 4,212,079 | 7/1980 | Segar et al. | 364/900 |
| 4,380,802 | 4/1983 | Segar et al. | 364/900 |
| 4,575,804 | 3/1986 | Ratcliff | 364/715 |

*Primary Examiner*—Thomas M. Heckler
*Assistant Examiner*—John G. Mills

*Attorney, Agent, or Firm*—Chernoff, Vilhauer, McClung & Stenzel

[57] ABSTRACT

The present invention relates to a method and apparatus for preparing a series of daily menus that include foods having preselected characteristics. The menus are prepared from a list containing numerous food items, the caloric content of each item, which food group each item resides, and the applicability of each item for a particular meal. The daily menus are created from the items in the list in a manner such that each meal in each menu only includes items which are applicable to that meal, each meal has items from each of a preselected number of food groups, and each meal has a predetermined caloric content. After the menus are formed, selected items in the menus can be replaced, with each replacement item being applicable for the particular meal, being in the same food group, and having the same caloric content as the item that is replaced. The apparatus is an electronic digital computer which is programmed to automatically generate the menus for a particular gender and desired weight loss of the user, and then provide replacement items for particular items in the menu which satisfy the foregoing characteristics at the request of the user.

3 Claims, 1 Drawing Sheet

APPARATUS FOR GENERATING A BALANCED CALORICALLY LIMITED MENU

BACKGROUND OF THE INVENTION

This invention relates to an apparatus for providing a menu according to a predetermined balanced and calorically limited diet, and in particular to such an apparatus which is simple to operate and which does not require a detailed understanding of the principles upon which the diet is based.

While the number of diets which have been developed is nearly unlimited, most of them are based on a common principle. First, every meal has a caloric level which depends on the sex, size, and desired weight loss of the dieter. Second, each meal has a selected number of foods from pre-selected food groups in order to obtain the desired nutritional balance. Finally, foods are chosen for each meal which are appropriate for that meal.

While this principle is quite simple and straightforward, creating a menu which meets these criteria and still satisfies the taste or inclination of the dieter requires long lists of foods and intricate calculation schemes which most dieters feel are so burdensome that they choose not to stick to the diet. This is because there are several unrelated characteristics of each food item which must be considered in determining how a particular food item fits into a diet, and the interaction of those characteristics makes the formulation of a menu which satisfies all of the necessary criteria a complex project. While charts and tables have been provided to assist in preparing a balanced, calorically limited, and individually pleasing menu, these aids are difficult to understand and, for many dieters, do not provide much assistance in planning meals.

SUMMARY OF THE INVENTION

The present invention overcomes the difficulties and limitations associated with prior art diets by providing an apparatus containing a computer which is programmed to make the necessary decisions in selecting food items for a menu according to a particular diet. Thus, the user only has to focus on the purely subjective criteria of what food items are appealing and the apparatus insures that the other criteria are followed. The apparatus has a visual display in which food items are presented for approval and a computer controlled menu is presented to assist the user in utilizing the apparatus, and a printer which provides the menu and other information in printed form.

Upon being prompted the user inputs into the apparatus his or her sex and the particular level of diet which is desired. The computer is programmed to provide daily menus for a one week period in which each meal includes only foods which are appropriate for that meal, is balanced with respect to food groupings according to a predetermined schedule, and is calorically limited based on the sex and diet level inputted. The user has the option of changing any item in any meal, with the apparatus displaying for review all of the options which are available within the established diet criteria for each item requested.

Once the weekly menu has been determined, the apparatus can provide a shopping list showing all of the items which are on that week's menu and the quantity of each.

The computer is programmed by means of a chip which is easily replaced. Thus, other diets can be provided having different food items, different food groupings or different caloric levels merely by changing the chip.

Accordingly, it is a principal object of the present invention to provide an apparatus which will assist the user to prepare a balanced, calorically limited menu which follows a particular diet and which appeals to his or her particular taste.

It is a further object of the present invention to provide such an apparatus which is simple to operate and which does not require the user to understand the principles upon which the diet is based.

It is a further object of the present invention to provide such an apparatus which allows the user to freely substitute more desirable food items without altering the balance or caloric content of the menu.

It is a still further object of the present invention to provide such an apparatus which provides a full week's menu in printed form.

It is a still further object of the present invention to provide such an apparatus which also can provide a grocery list showing all of the food items specified in the week's menu and the quantites of each.

The foregoing and other objectives, features and advantages of the present invention will be more readily understood upon consideration of the following detailed description of the invention taken in conjunction with the accompanying drawings.

DETAILED DESCRIPTION OF THE INVENTION

Figure 2:
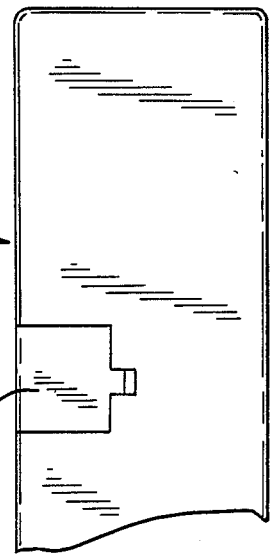
FIG. 2 is a fragmentary bottom view, at an enlarged scale, showing a portion of the apparatus.
Figure 1:
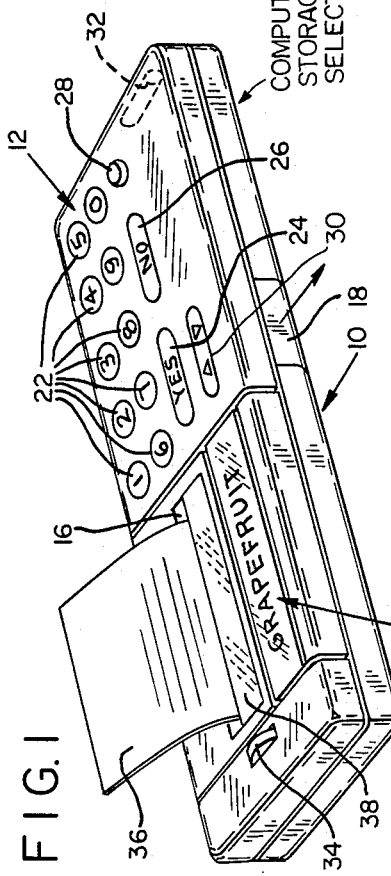
FIG. 1 is a perspective view showing the apparatus of the present invention.
Figure 3:
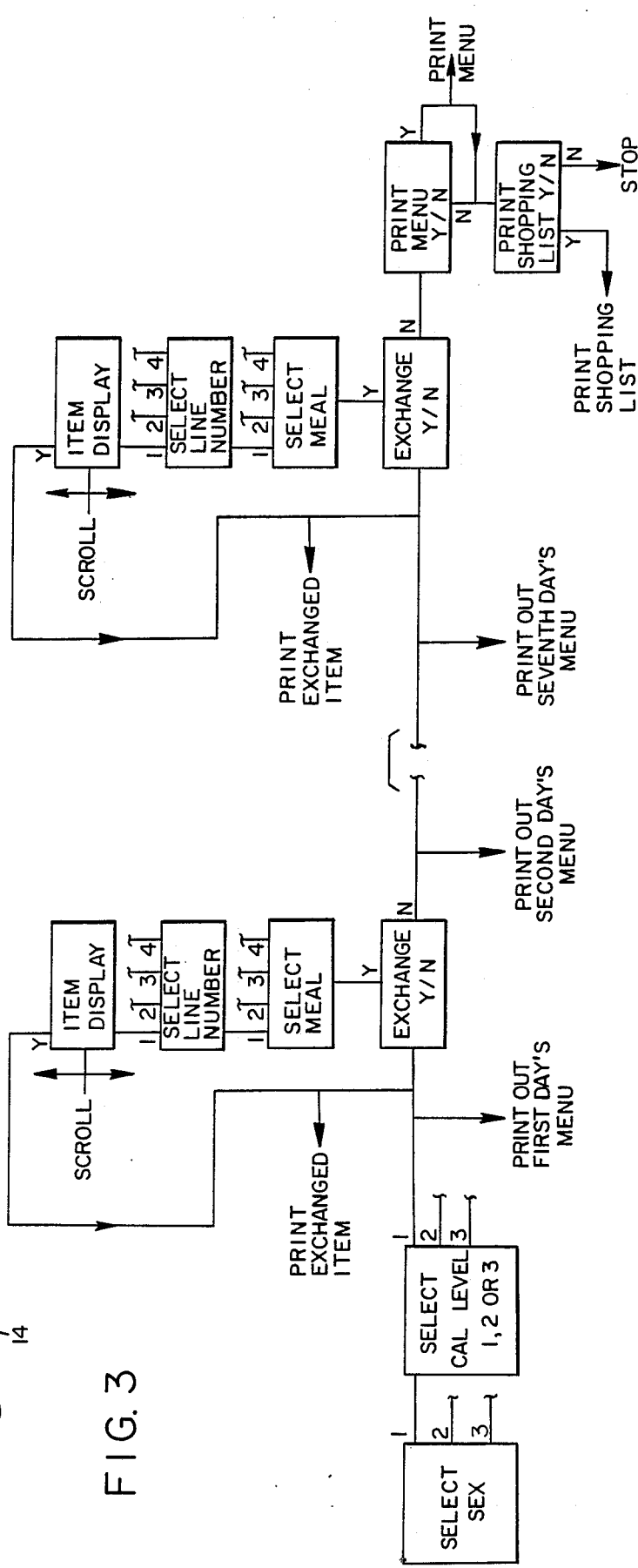
FIG. 3 is a flow chart showing how the apparatus operates.

Referring to FIG. 1 of the drawings, the apparatus of the present invention preferably is housed in a handholdable case 10 having a keyboard 12, a display 14 and a printer tape feed opening 16. The case enclosed an electronic computer and a printer (not shown) which are commercially available or which can easily be assembled from commercially available components by one skilled in the art, given the tasks which must be performed by the apparatus as set forth below. The case includes a removable cover 18, FIG. 2, which facilitates replacement of the program chip (not shown) that contains the computational instructions for the computer.

In the embodiment illustrated, the keyboard 12 includes ten numerical keys 22, a "yes" key 24, a "no" key 26, a "clear" key 28 and a "scroll" key 30. As will be more fully explained later the numerical keys serve multiple functions, and, if desired, these functions can be printed on the face of the keyboard below the appropriate key. A power switch 32 on the side of the case interconnects the computer and printer with a power source, which preferably is a wall mount AC-DC transformer (not shown). A thumb wheel 34 allows the printer paper 36 to be advanced manually, and a window 38, located adjacent to the tape feed opening 16, allows the tape to be immediately after it has been printed. The display 14 comprises a twenty character alpha-numeric LED display which preferably is approximately 5 mm high.

The apparatus creates a weekly menu with either three or four meals a day, by storing a list of applicable food items along with several characteristics of each item on the list. First, each item is categorized in regard to its applicability for a particular meal. Many items may be appropriate for more than one meal and, if so, each applicable meal will be listed for that item. Each item also is categorized as to which food group it falls into (e.g.,), meat, dairy products, vegetable, fruit, bread, and cereal. Finally, the caloric content of each item is listed. This characteristic, of course, depends on the size of the serving, and, several typical servings sizes and associated caloric content are typically listed for each item. Also input into storage is the appropriate calorie content for each meal for several levels of daily caloric content for men, women and children. In the embodiment illustrated, three overall levels of caloric content are provided, however, more or less could be used.

The computer is programmed according to techniques well known in the prior art to perform the sequence shown in the flow chart and described in the following description of how the apparatus operates. The program is on a chip (not shown) which is replaceable through the cover 18. Thus the apparatus can be used for other diets in which food items are selected as a result of grouping selected characteristics of the items.

When the apparatus is turned on the words "SELECT SEX" are displayed on the display 14. In response, the user depresses numerical key 1 for a man, 2 for a woman or 3 for a youth. The program then selects a first category of caloric level accordingly, and the words "SELECT CAL LEVEL 1, 2 OR 3" are displayed to indicate the desired caloric level within the particular sex group which was selected. After the user has selected a level, by pressing the appropriate numerical key, the computer selects a predetermined number of food items from each category in preselected food groups to create a first day's menu having the appropriate balance and calorie content. This first day's menu then is printed onto the tape 36. By way of example the apparatus might be programmed to provide three meals per day, breakfast, lunch and dinner, with four items for breakfast, five items for lunch and five items for dinner. The breakfast items might include one meat, one cereal, one fruit and one dairy product; the lunch items two fruits, one meat, one vegetable, and one bread; the dinner items two meats, one fruit and two vegetables. At the selected sex and level, breakfast would have X calories, lunch Y calories and dinner Z calories. The day's menu would include four breakfast items having X calories and including one meat, one cereal, one fruit and one dairy product; five lunch items having Y calories and including two fruits, one meat, one vegetable and one bread; and five dinner items having Z calories and including two meats, one fruit, and two vegetables.

After the first day's menu is printed the apparatus displays the words "EXCHANGE: Y/N" on its display. If the user is satisfied with that day's menu he presses the "No" button 26 and the computer selects a second day's menu and the process is repeated. On the other hand, if the user desires to change any item on the first day's menu, he presses the "Yes" button 24. The words "SELECT MEAL" are then displayed giving the user the option of choosing which meal he or she would like to make a change in. The user then selects the appropriate meal by depressing numerical key 6, 7, 8, and 9 for breakfast, lunch, dinner or snack, respectively. The words "SELECT LINE NUMBER" is then displayed and the user presses the numerical key which designates the line in which the food desired to be changed lies. The computer then selects a substitute food item from the same category and food group and having the same caloric content as the selected food item and shows it on the display. The user can review all of the possible options available as a substitute for that item by depressing the "Scroll" button thereby causing the apparatus to sequentially display all of the possible food items from the same category and food group and having the same caloric content. When the desired item is displayed it can be substituted into the menu by depressing the "Yes" key. The words "EXCHANGE: Y/N" will then be displayed again and the process will be repeated to replace other food items. Once the entire day's menu is satisfactory the "No" key is depressed and the computer selects and prints out a second day's menu. The foregoing exchange process is then completed for the second day's menu and the third day's menu is selected.

This process is repeated until the full week's menu is completed, at which time the words "PRINT MENU Y/N" is displayed. The user then can have the full week's menu, which has been developed by the foregoing substitution process, printed by depressing the "yes" key. In some cases, such as where little or no substitutions were made, the daily menus which already have been printed will suffice. In this case, the user depresses the "No" key. In either event the words "PRINT SHOPPING LIST Y/N" are then displayed. If the "No" key is depressed, the program is terminated. If the "Yes" key is depressed, the apparatus prints out a shopping list showing all of the items on that week's menu and the required quantities of each item. Once the shopping list has been printed the program terminates.

Any command which is made by the user can be cancelled by immediately depressing the "Clear" key 28.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. An electronic digital computer for preparing a balanced calorically limited diet, said calculator comprising:
    (a) a memory from which data can be retrieved, said memory having stored therein a list of food items, the caloric content of each of said items, in which of a selected number of food groups each of said items resides and the applicability of each of said items for a particular meal;
    (b) means for generating a daily menu for a selected period of time from said items in said list with eaach meal in said menu only having foods which are applicable for the meal, which are from particular predetermined ones of said food groups and which have particular caloric content; and
    (c) means for replacing items in each meal on said menu, with each replacement item being applicable to the same meal, being in the same food group, and having the same caloric content as the item it replaced.

2. The calculator of claim 1 wherein said means for generating a daily menu includes means for tailoring the caloric content of said menu depending upon the gender and desired rate of weight loss of the user, including means for inputting said gender and said rate into the apparatus.

3. A method for preparing a menu having balanced food groups and a predetermined caloric content using a digital computer, comprising:

(a) providing a memory for said computer, having stored therein a list of food items, the caloric content of each of said items, in which of a selected number of food groups each of said items resides, and the applicability of each of said items for a particular meal;

(b) generating daily menus for a selected period of time from items in the list, with each meal in each daily menu having foods which are applicable for that meal, having foods from particular ones of said food groups, and having a particular caloric content; and (c) replacing selected items on said daily menus with replacement items from said list with each replacement item being applicable to the same meal, being in the same food group, and having the same caloric content as the item it replaced.

* * * * *

UNITED STATES PATENT AND TRADEMARK OFFICE
CERTIFICATE OF CORRECTION

PATENT NO.    : 4,954,954
DATED         : September 4, 1990
INVENTOR(S)   : Lamar R. Madsen, et al.

It is certified that error appears in the above-identified patent and that said Letters Patent is hereby corrected as shown below:

Col. 2,   Line 46:   Change "enclosed" to --encloses--.

Col. 2,   Line 67:   Insert --read-- after "be".

Col. 4,   Line 61:   Change "eaach" to --each--.

Col. 4,   Line 62:   Change "the" to --that--.

Signed and Sealed this

Fourteenth Day of July, 1992

*Attest:*

DOUGLAS B. COMER

*Attesting Officer*    Acting Commissioner of Patents and Trademarks